US005888752A

United States Patent [19]

Malin et al.

[11] Patent Number: 5,888,752

[45] **Date of Patent: *Mar. 30, 1999**

[54] UNIVERSAL RINSE REAGENT AND METHOD FOR USE IN HEMATOLOGICAL ANALYSES OF WHOLE BLOOD SAMPLES

[75] Inventors: Michael J. Malin, Park Ridge, N.J.; Phyllis Shapiro, Yorktown Heights, N.Y.

[73] Assignee: Bayer Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 442,363

[22] Filed: May 16, 1995

[51] Int. Cl.[6] .......................... G01N 33/50; G01N 33/53; C11D 3/48

[52] U.S. Cl. ............................ 435/7.24; 422/1; 435/7.25; 435/962; 436/546; 436/8; 436/49; 510/161

[58] Field of Search ................................ 435/7.24, 7.25, 435/962; 422/1; 436/546, 8, 63, 49; 252/106, 174.21–174.23; 424/78.17; 510/161

[56] References Cited

U.S. PATENT DOCUMENTS

| | | | |
|---|---|---|---|
| 3,893,936 | 7/1975 | Hubele | 252/106 |
| 4,102,810 | 7/1978 | Armstrong . | |
| 4,311,618 | 1/1982 | Schafer-Burkhard . | |
| 4,384,971 | 5/1983 | Carter, II et al. | 252/106 |
| 4,528,274 | 7/1985 | Carter et al. . | |
| 4,595,524 | 6/1986 | Yip et al. | 252/408.1 |
| 4,745,071 | 5/1988 | Lapicola et al. . | |
| 5,035,859 | 7/1991 | Gu et al. | 422/28 |
| 5,227,304 | 7/1993 | Wong . | |
| 5,250,438 | 10/1993 | Ryan | 436/17 |
| 5,639,630 | 6/1997 | Malin et al. | 435/28 |

FOREIGN PATENT DOCUMENTS

| | | |
|---|---|---|
| 0 471 293 A2 | 2/1992 | European Pat. Off. . |
| A-56 045 998 | 4/1981 | Japan . |

*Primary Examiner*—James C. Housel
*Assistant Examiner*—James L. Grun
*Attorney, Agent, or Firm*—Morgan & Finnegan, LLP

[57] ABSTRACT

The present invention provides a heretofore unknown use for a aqueous reagent composition that serves as a universal rinse for performing and/or improving a variety of hematological analyses on automated analyzers. The universal rinse reagent comprises a phosphate buffer to maintain the rinse solution pH at from about 7.0 to about 7.6; a nonhemolytic nonionic surfactant, such as a Pluronic® an alkali metal salt, such as NaCi; antimicrobial and anti-oxidant compounds; and has an osmolality of about 285 to 305 mOsmol/kg. The universal rinse reagent composition is highly suitable for use in the rinse phases or cycles of all types of blood cell analysis methods and processes performed on semi- and fully-automated systems. The invention allows the replacement of mutiple and specific rinse solutions with the disclosed universal rinse to obtain accurate and acceptable results, independent of the types of blood cell analyses that are performed. The universal rinse is most particularly useful for automated systems having intricate hardware and a number of different input and output channels. The universal rinse composition serves to economize, streamline, and simplify the design and operation of such systems.

35 Claims, 1 Drawing Sheet

Px R1 Reagent:
0.105 g/L SDS

Rinse: 2.0 g/L SDS

Rinse: 2.0 g/L SDS + 3.0 g/L Brij® 35

Rinse Carryover Volume (µL): 7.9

7.9

Rinse Carryover Volume (µL): 10.1

10.1

Rinse Carryover Volume (µL): 13.3

13.3

UNIVERSAL RINSE REAGENT AND METHOD FOR USE IN HEMATOLOGICAL ANALYSES OF WHOLE BLOOD SAMPLES

FIELD OF THE INVENTION

The present invention relates to the analysis of whole blood samples using automated hematology systems and a reagent composition employed therein for assurance of accurate and precise results of blood cell analyses performed, low background noise, and optimal operativity and cleanliness of the automated system.

BACKGROUND OF THE INVENTION

The use of semi- and fully-automated analyzer systems for the quantification, identification, and characterization of the cells in whole blood aids in the efficiency and economy of performing all types of hematology analyses known in the art. Automated systems are used in the analysis of a variety of both normal and abnormal counterparts of all blood cell types, for example, red blood cells (erythrocytes), reticulocytes (immature erythrocytes), white blood cells (leukocytes), platelets, and in the determination of many parameters related thereto. For example, mean cell volume and hemoglobin concentration and content are characteristics of red blood cells which are routinely measured.

Problems in the art arise due to lack of accuracy, precision, and reproducibility of the final results, which may stem from cell contamination due to inefficient and/or suboptimal methods and reagents, as well as from accumulated build-up of reagents in the sample chambers and system hardware, especially when hundreds of samples are processed and analyzed in rapid fashion.

Although automated hematology processes and automated flow systems therefor have been developed to ease the burden of all types of blood cell analysis, the processes and systems must be continously cleaned and kept in optimal working order to insure reliable, accurate, and efficient operativity and results. Specific examples of the various types of hematology analyses, methods, and improvements thereof, that are performed using automated systems include differential white blood cell counting, such as described in U.S. Pat. No. 3,741,875 to Ansley et al.; U.S. Pat. No. 4,099,917 to Kim; and U.S. Pat. Nos. 4,801,549 and 4,978,624 to Cremins et al.; blood cell and reticulocyte analyses, including the analysis of a variety of characteristics of these cell types, such as described, for example, in U.S. Pat. No. 5,350,695 to G. Colella et al., U.S. Patent Nos. 5,360,739 and 5,411,891 to S. Fan et al., U.S. Pat. No. 4,735,504 to Tycko, and in C. Brugnara et al., 1994, Am. J. Clin. Path., 102(5):623–632. Many of the automated hematology systems rely on electrooptical measurements and absorbance/light scatter or fluorescence/light scatter flow cytometry techniques to obtain and present the final results as cytograms or useful output.

In general, for the performance of each type of hematology analysis performed using an automated system, the system is designed to have several different channels which are responsible for carrying out distinct functions during the analysis and/or displaying information about individual cell types or the particular parameters being measured. As a consequence of the various operational channels and the numbers of samples to be routinely processed, the automated systems, including all sample chambers, and the system hardware, including channels, pumps, tubing, valves, containers, joints, and the like, must be routinely rinsed with one or more reagent solutions to avoid build-up and contamination by the reaction mixture, which comprises the blood sample and other reagent components, after repeated aspirations of the samples and the sample reagent solutions undergoing rapid analysis. A particular example is demonstrated by current automated hematology analyzer systems, such as those commercially available under the trade designation TECHNICON H●™, e.g., H●1™, H●2™, and H●3™, and the like, and sold by the assignee of the present invention, in which more than one type of rinse reagent is used, depending on the type of analysis being performed. As more particularly exemplified, the aforementioned hematology systems generally require one type of rinse reagent formulation for the hemoglobin (i.e., Hb) and red blood cell/platelet (i.e., RBC/PLT) channels, and a different type of rinse reagent for the peroxidase and basophil channels used in performing hematology analyses.

As indicated, problems and interference result from the carryover of one reaction mixture into another reaction mixture in the chambers of automated analyzers, particularly when the chambers are used again and again for multiple sample analyses. By reaction mixture is meant a whole blood sample mixed with a reagent composition comprising appropriate concentrations or amounts of reagent components.

Rinse solution carryover, when it contributes reactive chemical components, such as lytic surfactant, to a reaction mixture undergoing analysis in a method (i.e., when it "participates" in any way in a reaction mixture) may adversely affect the analytical results and lead to erroneous, inaccurate, and imprecise determinations and cytogram readings. That rinse carryover varies from system to system also presents problems and adversely affects the results of and information obtained from an analytical method. For example, too little rinse carryover volume in a method can result in excess noise at the origin of cytograms. Alternatively, excess rinse carryover volume in a method can cause the white blood cells to be attacked by the presence of active lytic surfactant in the carryover volume. Such adverse effects compromise the accuracy and reliability of hematological results, particularly, for example, in the peroxidase method of white blood cell differential counting performed on automated hematology analyzers.

Thus, there is a clear need in the art for improved rinse reagent solutions or diluents for use in methods in which blood samples are processed and analyzed using automated hematology systems. Such reagent solutions and methods using such reagent solutions are needed to thoroughly cleanse all of the reagent chambers, the channels, and other mechanical hardware of the automated analyzers (e.g., the system hydraulics, including pumps, tubing, valves, and the like) following aspiration of the samples from the chambers to remove residual debris and to alleviate the formation of buildup in the hydraulic path. Also, such reagents and methods would fulfill the need to maintain the optimum integrity of the resulting cytograms after many rounds of sample analysis. Also needed in the art are reagents that are capable of simplifying the design and operation of automated hematology systems, which are frequently quite versatile and suitable for several different types of hematology methods and procedures for performance on such systems. A further need in this art is the elimination of unecessary redundancy of reagents, particularly rinse reagent solutions, for economy and for the streamlining of blood sample analyses.

Reagent compositions have historically been developed for use in automated systems for very specific purposes. As is conventional in the art, a reagent composition formulated, tested, and used over time to achieve a particular purpose and to perform a particular function in a system, is recognized and routinely used in the art solely for that purpose and function in that system. Thus, under routine circumstances, a reagent composition, which is optimized for a particular purpose and function, is appreciated, used, and most frequently taken for granted by those in the art based on its known and intended purpose and for no other purpose. It is only rarely and unexpectedly that a reagent or material designed and used for a specific purpose in the art happens to be found useful in a completely different way and/or for a completely different and unique purpose that is unrelated to its original and intended use. Such a new use or application of a reagent is neither expected nor predicted by those having skill in the art.

An example of one reagent composition used routinely to perform a particular function on automated hematology systems is known as a red blood cell/basophil sheath ("RBC/Baso sheath"). The RBC/Baso sheath was designed for use on the abovementioned automated analyzers of the TECHNICON H●™ series to surround the sample stream by a concentric layer of liquid to prevent the cells in the reaction mixture sample streams of the red blood cell and basophil channels from contacting or touching the walls of the analyzer flow cell. The sheath is thus a "passive" or noninteractive reagent, since it does not physically interact with blood cells to any significant degree; it was not designed or used to contact samples. The sheath contains a surfactant in order to prevent the formation of bubbles which interfere with the automated methods by causing the sample stream to wander out of alignment, thereby producing distorted optical registration by the detector. Other ingredients in the RBC/Baso sheath reagent are phosphate buffered saline having an osmolality of about 290 mOsmol/kg and an antioxidant to protect the surfactant from autooxidation. The osmolality of the sheath reagent was designed to be isotonic to red blood cells so that their mean cell volumes would not change if there was inadvertent contact between blood cells in the sample stream and the sheath surrounding the sample stream. A preferred surfactant, Pluronic® P105, is present in the sheath reagent at a concentration that is nonlytic to red blood cells, in case there was unexpected contact between cells in the sample stream and in the surrounding sheath stream.

The RBC/Baso Sheath conventionally operates in a closed system as follows: the Sheath is introduced into the RBC/Baso flow cell by negative pressure from a syringe pulling the sheath out through the top of the flow cell, at the same time that a larger positive pressure diaphragm pump delivers the sheath through a concentric flow module at the bottom of the flow cell. The sample stream enters the concentric flow module at a different point. The velocities of the optically transparent sheath fluid and the sample stream (which have the same refractive indexes) are controlled so that laminar flow (i.e., non-turbulent) conditions exist. The sample and the sheath streams flow independently through the flow cell. It is the hydraulic pressure of the sheath stream that constricts the sample stream to its appropriate diameter. Thus the sheath performs its function of protecting the sample stream from touching the parts of the automated system hardware.

However, prior to the present invention, neither the RBC/Baso sheath nor other reagents employed to perform their particular functions in automated hematology analyzers have been recognized or used for the purpose of a rinse solution having universal applicability to all types of blood cell analysis. Thus, there is still a need extant in the art for providing a universally applicable reagent that can be used as a rinse reagent to keep systems free of buildup over extended periods of continous and varied operations. The use of such a widely-acceptable reagent promises to simplify and streamline the designs of current systems, to alleviate background noise caused by unwanted cell debris generated during the performance of hematology methods, and to generally improve the operativity of automated systems used in the field of blood sample analysis.

SUMMARY OF THE INVENTION

The present invention provides the use of a universal reagent composition in methods to quantify and differentiate populations of cell types in fresh and aged whole blood samples. The invention is particularly suitable for use as an intersample rinse in electro-optical procedures and flow cytometry analysis.

It is an object of the present invention to provide the novel use of an aqueous reagent composition in semi- and fully-automated hematology systems to avoid the problems of carryover of unwanted reaction mixture components from one method step to another, thus allowing for clean separation and quantification of cell types and the prevention of the generation of unacceptable levels of sample buildup in the system hardware and background noise in the cytograms resulting from the method.

It is another object of the invention to provide a heretofore unrecognized and therefore unknown use for a reagent described in accordance with its use herein as a universal intersample rinse reagent to simplify and streamline the design and operation of different types of hematology analyses performed on automated hematology systems with a variety of blood sample types, e.g., aged and fresh blood samples, abnormal and normal blood samples, and samples stored in both the cold and at room temperature.

Yet another object of the invention is to provide an aqueous univeral reagent composition that is compatible for use in all hematology methods involving whole blood samples and performed on automated systems.

Still another object of the invention is to provide a reagent composition used as a universal rinse that is able to reduce the total number of washing and/or rinsing reagents presently required for cleansing system hardware and for eliminating carryover in automated analyzers.

Another object of the invention is to provide a use for a reagent composition as a universal rinse reagent solution that is wholly and universally compatible with any wash reagents used in automated hematology systems and parts thereof.

Further objects and advantages afforded by the invention will be apparent from the detailed description hereinbelow.

BRIEF DESCRIPTION OF THE DRAWINGS

In the appended drawings of the figures, which are presented to further describe the invention and assist in its understanding through clarification of its various aspects.

DESCRIPTION OF THE DRAWINGS

Figure 1A:
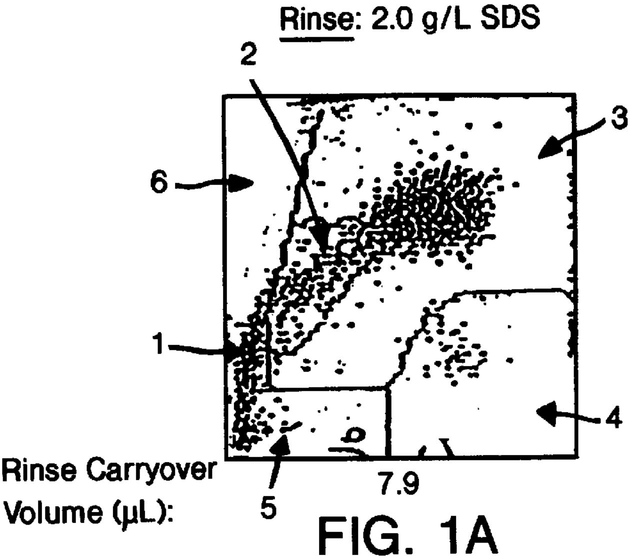
FIGS. 1A–1F depict cytograms obtained when various reagent solutions or diluents prepared as described and in accordance with the present invention were utilized in the determination of differential white blood cell counts using the electro-optical detection system of an automated hematology analyzer.
Figure 1B:
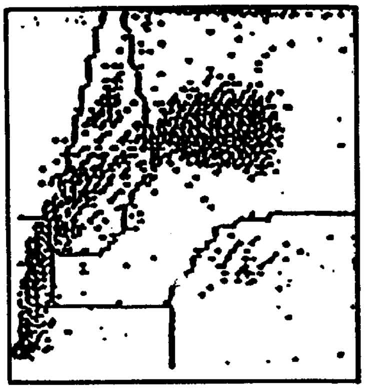
Figure 1C:
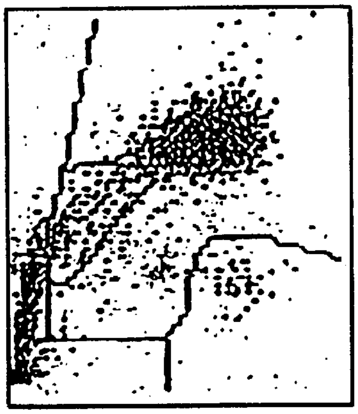
Figure 1D:
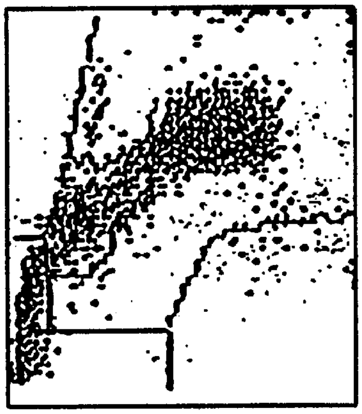
Figure 1E:
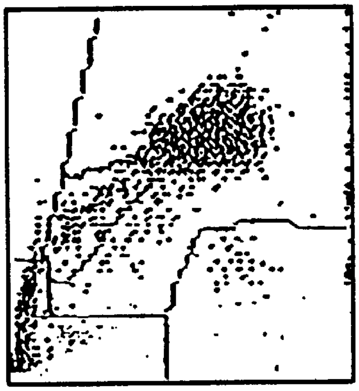
Figure 1F:
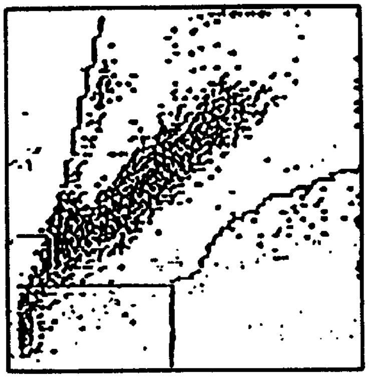

The numerical labels as depicted in FIG. 1A serve to identify the different regions of the cytogram and are identical in each of the figures. As shown, number 1 indicates the area of the lymphocyte population; number 2 indicates the area of the monocyte population; number 3 indicates the area of the neutrophil population; number 4 indicates the area of the eosinophil population; number 5 indicates the area of origin noise arising from platelets and red cell ghosts; and number 6 indicates the area of the population of large unstained white cells or LUCs. FIGS. 1A–1F are cytograms depicting the results of experiments performed to test the effects of variable rinse carryover on white cell differential counts using the peroxidase method of white blood cell differential analysis, comprising a sample cycle which includes an intersample rinse employing an aqueous rinse reagent composition. The rinse carryover volume is shown beneath FIGS. 1A–1F: FIGS. 1A and 1B demonstrate the results of a rinse carryover volume of 7.9 μL; FIGS. 1C and 1D demonstrate the results of a rinse carryover volume of 10.1 μL; and FIGS. 1E and 1F demonstrate the results of a rinse carryover volume of 13.3 μL. The R1 reagent solution of the peroxidase method contained 0.105 g/L SDS (see Example 1). As shown at the top of the figure, two aqueous rinse reagent compositions were used in the peroxidase method. Cytograms resulting from a standard rinse solution containing 2.0 g/L SDS are shown in FIGS. 1A, 1C, and 1E. Cytograms resulting from a rinse solution containing 2.0 g/L of SDS and 3.0 g/L of Brij® 35 are shown in FIGS. 1B, 1D, and 1F. The FIG. 1A–1F results show that the presence of Brij® 35 in the rinse is detrimental to high quality results if the rinse carryover volume exceeds approximately 8.0 μL.

DETAILED DESCRIPTION OF THE INVENTION

The present invention provides advantages to the art of hematology analysis using automated systems. The invention relates to the use of a reagent composition as a universal intersample rinse reagent solution capable of improving the performance and efficiency of al types of automated hematology methods. The invention relates particularly to semi- and fully-automated flow cytometric analyzers used in the measurement and differentiation of both red and white blood cells and their precursors, and in the determination of various characteristics of various populations of blood cells in whole blood samples. Use of the universal rinse reagent also solves annoying problems routinely encountered in the art, for example, having to use several different rinse reagents to remove reaction mixture debris that accumulates in the hydraulic paths of automated systems during multiple sample analyses. Thus, the use of the universal rinse reagent of the invention both simplifies the design of automated systems and alleviates the need for multiple rinse agents of different types.

In addition, a reagent solution formulated with nonlytic nonionic surfactant was recognized and used for the first time by the present inventors as a universal "rinse" reagent solution capable of being employed in all types of hematology procedures performed on automated analyzers. The use of this type of rinse composition prevents variations in rinse carryover volume from adversely affecting the results of the hematological methods, as occurs in FIGS. 1D and 1F. The nonhemolytic surfactant component of the universal rinse reagent composition of the invention is capable of providing sufficient detergency to prevent the formation of buildup, while at the same time, not attacking or destroying the blood cells in the sample undergoing analysis.

As a specific yet nonlimiting example, the rinse reagent was found to be particularly effective in reducing origin noise when used in conjunction with a novel reagent composition containing both a nonionic polyethyoxylate surfactant (e.g., Brij® 35) and an ionic surfactant (e.g., SDS or TDAPS) in the first reaction phase (i.e., the cell lysis and fixing phase) of the peroxidase method of white cell differential counting. The use of the universal rinse in the peroxidase method was also found to solve the problem of system-to-system variability due to rinse carryover that had previously plagued those who have performed repeated peroxidase analyses on automated systems. Rinse carryover impacts on the position of cell clusters in the cytograms generated as a result of the automated flow cytometry analysis. The use of the rinse solution, which was free of nonionic surfactant such as Brij® 35, also afforded improvement of the results obtained using blood samples stored at room temperature for 24 hours.

The aqueous rinse reagent composition formulated and used in accordance with the invention was newly determined to have universal applicability and compatibility with all types of blood cell analyses performed on automated analyzers. This universal rinse reagent is optimally designed to be used between samples as an intersample rinse to remove reaction mixtures comprising previous samples mixed with reagents that are routinely left over in analyzer reaction chambers and channels after the samples are aspirated. Used as a universal rinse solution, the rinse reagent was discovered to be able to reduce the total number of reagents, including rinses, sheaths, and washes, that are required for the optimum performance for automated hematology systems. It is envisioned that the universal rinse can replace multiple rinse reagents or solutions that are presently used in automated systems for numerous types of hematological analyses; a nonlimiting example of such automated hematology analyzers are the commercially available TECHNICON H●™ series.

The components of the rinse reagent, which was discovered to be an effective universal rinse as first disclosed herein, are formulated in aqueous admixture. In its simplest formulation, the rinse reagent of the invention comprises a phosphate buffer (e.g., phosphate buffered saline, pH of about 6.8 to 7.8) and a nonionic and nonhemolytic surfactant of the Pluronic® family or class of surfactants. In general, Pluronic® surfactants are block copolymers of polyoxyethylene and polyoxypropylene of the structure: $(EO)_x$—$(PO)_y$—$(EO)_x$ (see Pluronic® & Tetronic® Surfactants, BASF Corporation, Parsippany, N.J., 1987). Pluronic® surfactans are formed by synthesizing the polypropylene glycol unit, $(PO)_y$, by controlled polymerization of propylene oxide. Next, EO polymeric chains are formed on both sides of the poly(PO) unit to yield the Pluronic® copolymer. Those in the art are aware that EO polymerization can be controlled symetrically so that "x" is essentially the same on each side or end of the Pluronic® molecule.

The polyoxypropylene block ($(PO)_y$) of the Pluronic® surfactants can have a molecular weight of about 950 to 4000 grams and comprise from about 20% to 90%, by weight, of the surfactant molecule. Pluronic® surfactants suitable for use in the invention have %EO values, by weight, in the range of about 20 to 80% by weight, with a molecular weight range for the polyoxypropylene block from about 2000 to about 4000 g/mol. More preferred is a %EO in the range of about 30 to 70% by weight, with a molecular weight range for the polyoxypropylene block from about 3000 to about 3600. For example, Pluronic® P105 and P85 have %EO values of about 50%, by weight, and Pluronic® P104 and P84 have %EO values of about 40%, by weight. Nonlimiting examples of suitable Pluronic® surfactants are P84, P85, P103, P104, P105, and P123, with P105 being more preferred. P105 has a molecular weight of about 6500 and comprises about 50% polyoxyethylene, by weight. The use of such Pluronic® surfactants serves to clean the hydraulic path of the automated system by capturing hydrophobic material from the reaction mixture into surfactant micelles.

Those in the art should also be aware that the Tetronics® (i.e., tetra functional block copolymers derived from the sequential addition of propylene oxide and ethylene oxide to ethylenediamine) have cationic properties due to the presence of tertiary nitrogens in the molecule. Accordingly, such cationic characteristics of Tetronics® are not suitable in the present invention, because of compatibility problems (i.e., precipitation) with the ionic surfactant, e.g., SDS, present, for example, in the reaction 1 reagent solution of the peroxidase method of leukocyte differential counting.

The rinse reagent also contains an agent or compound to retard microbial growth. Examples of suitable anti-microbial compounds include, but are not limited to Proclin 150 (2-methyl-4-isothiazolin-3-one) and Proclin 300 (5-chloro-2-methyl-4-isothiazolin-3-one) (Rohm & Haas); Germall 115 (N,N'-methylenebis[N'-(1-(hydroxymethyl)-2,5-dioxo-4-imidazohdinyl] urea) (Sutton laboratories); Dowacil 200 (1-(3-chloroallyl)-3,5,7-triaza-1-azoniaadamantane chloride) (Dow Chemical); and Bronopol 2-bromo-2-nitropropane-1, 3-diol ($C_3H_6BrNO_4$) (Angus Chemical Company), with Proclin 150 being preferred. Also included in the rinse reagent are one or more buffering compounds or mixtures thereof, for example, monobasic sodium phosphate and dibasic sodium phosphate, to maintain a neutral or near-neutral pH of the final solution. An alkali metal chloride salt, such as NaCl, LiCl, KCl, and the like, may also comprise the rinse reagent, with NaCl being preferred. A water-soluble antioxidant is also present in the rinse solution to stabilize the non-hemolytic surfactant against anti-oxidation. Examples of suitable antioxidants include, but are not limited to, 3, 3'-thiodiproprionic acid; 3', 3'-dithioacetic acid; Trolox® (i.e., water-soluble vitamin E, Hofftnan-LaRoche); BHT, butylated hydroxytoluene or 2, 6-di-tert-butyl-4-methylphenol; BHA, butylated hydroxyanisole or 2-tert-butyl-4-methoxyphenol; and MEHQ or ρ-methoxyphenol, or mixtures thereof. As indicated, the rinse reagent composition includes suitable buffers to maintain the pH of the reagent composition from between about 6.8 to about 7.7, more preferably about 6.9 to about 7.5, and most preferably about 7.0 and about 7.3. The final osmolality of the solution is from about 275 mOsm/kg to about 320 mOsm/kg, more preferably about 285 mOsm/kg to about 305 mOsm/kg. In addition, the final rinse reagent solution may be filtered (e.g., 0.2 $\mu$) to remove particulate matter which would otherwise be a potential source of buildup in the system.

Table 1 sets forth an exemplary formulation of the universal rinse reagent composition, including the amounts, and ranges thereof, of each rinse reagent component to yield the appropriate and operative pH and osmolality of the final universal reagent solution. For each of the components of the rinse reagent composition as listed in Table 1, the preferred quantities per liter are provided in parenthesis, and are not intended to be limiting. It will be appreciated by those in the art that the concentrations and ranges of each of the listed rinse solution components may deviate by about ±5% to 10% without adversely affecting the composition.

TABLE 1

| Component | Qty/L |
|---|---|
| Antimicrobial agent (e.g., Proclin 150) | 0.25 mL–0.60 mL (0.40 mL) |
| Nonhemolytic nonionic surfactant (e.g., Pluornic ® P105) | 0.50 g–1.5 g (1.00 g) |
| NaPhosphate, monobasic | 0.285 g–0.315 g (0.300 g) |
| NaPhosphate, dibasic | 2.28 g–2.52 g (2.40 g) |
| Inorganic salt (e.g., NaCl, KCl, or LiCl) | 7.40 g–8.0 g (7.70 g) |
| Antioxidant (e.g., 3,3'-thiodiproprionic Acid) | 0.050 g–0.150 g (0.100 g) |
| Deionized Water, q.s. to | 1.00 L |
| pH | 6.9–7.6 (7.0–7.3) |
| Osmolality (mOsmol/kg) | ≈ 285–305 mOsm (300 mOsm) |

As indicated, an inorganic salt may also be included in the reagent solution. Salts suitable for use in the present invention may be alkali metal chloride salts such as NaCl, KCl and LiCl. Sodium chloride, NaCl, is a preferred salt. The salt, when used, should preferably be present in an amount of from about 125 mM to about 136 mM. When NaCl is used as the salt, it is present in the reagent solution in an amount of from about 7.4 to about 8.0 g/L.

The buffer or mixture of buffers used in the rinse reagent should be suitable for maintaining the pH of the reagent solution from between about 6.8 to about 7.6, preferably from about 6.9 to about 7.5, and more preferably from about 7.0 to about 7.3. Suitable buffers include sodium or potassium phosphates, diethyl malonate, 3-(N-morpholino) propane sulfonic acid, MOPS), N-2-acetamido-2-aminoethane sulfonic acid (ACES), and 4-(2-hydroxyethyl)-1-piperazine-ethanesulfonic acid (HEPES). Preferred is a mixture of $Na_2HPO_4$ (sodium phosphate, monobasic) and $NaH_2PO_4$ (sodium phosphate, dibasic). As indicated, the buffers should be present in the reagent solution of this invention in an amount suitable to maintain the pH of the solution at approximately neutral levels. For instance, when a mixture of $Na_2HPO_4$ and $NaH_2PO_4$ is used, the mixture should contain a mole ratio of $Na_2HPO_4$ to $NaH_2PO_4$ which is from about 3.39:1 to about 6.76:1 to produce a series of solutions with a pH range of about 7.0 to about 7.3. The concentration of such a phosphate buffer mixture in the reagent solution of this invention is from about 0.020M to about 0.050M. In addition, it will be appreciated that the pH of the rinse reagent solution may be adjusted to achieve a pH in the physiological range using the appropriate proportions of conventional acids and bases (e.g., 3.0 N HCl and 4.0 N NaOH). Those skilled in the art will appreciate that as the concentration of the buffer increases, the concentrations of other components in the reagent composition must decrease accordingly, in order to maintain an acceptable osmolality range.

The rinse reagent solution to be used universally in the practice of hematology analyses and in accordance with the invention is an aqueous solution and, preferably, deionized water is used. The solution is prepared by combining the ingredients, in admixture, in water. A close watch should be maintained on the pH of the solution to ensure that it stays within the desired range. Those skilled in the art may also include other additives in the reagent solution as desired. For instance, ethylenediamine tetraacetic acid (EDTA), EGTA, disodium, trisodium, or tetrasodium EDTA or EGTA, may be included as a polyvalent metal ion chelator, which chelates and deactivates metal ions such as iron or copper that may catalyze auto-oxidation of the surfactant.

In addition, the rinse reagent solution of the invention removes intersample debris sufficient to assay at least about 500 to 1000 blood samples before a system wash is required (see Example 2), and maintains cleanliness of the system to allow the acceptable performance of all blood analysis methods.

The suitability of the rinse reagent as described herein for use as a universal rinse was demonstrated by employing the rinse reagent composition in a run that included 1035 aspirations of whole blood. During this run, the rinse maintained the cleanliness of the system so that all of the subsequent blood sample methods carried out on the automated analyzer performed in an acceptable manner and provided accurate and precise results. This suitability was also reproduced when the rinse reagent was four years old, thereby demonstrating the stability of the rinse reagent composition over time. It is recommended that the universal rinse reagent contact the entire hydraulic path of the system used in the automated hematology analysis, including as many of its individual parts as possible, to insure that debris has no chance to accumulate in any part of the system, such that the buildup cannot then be easily removed by using a wash reagent.

In optimizing the formulation of the universal rinse reagent, a variety of surfactant candidates were tested in a milieu which contained 0.5 mL/L of Proclin 150 in deionized water. The resulting rinse formulations were then tested in a number of different types of hematology analyses on automated systems. It was determined that ionic surfactants were not useful in the rinse composition. As specific examples, SDS (an anionic surfactant), if present in the rinse reagent formulation, was incompatible with the cationic dye, Oxazine 750, which is a component of a reagent used in the analysis of reticulocytes. CTAB (a cationic surfactant), if present in the rinse reagent formulation, interfered with the performance of the peroxidase method of white blood cell differential counting and subpopulation determination, presumably as a result of its incompatibility with SDS in the specific reagent diluent used in the first reaction phase of the of the peroxidase method of determining white blood cell differential counts. Lauryl dimethylamine N-oxide or LO, (a zwitterionic surfactant), if present in the rinse reagent formulation, interfered with the performance of the peroxidase method of white blood cell differential counting and subpopulation determination. Another zwitterionic surfactant, TDAPS, if present in the rinse reagent formulation, also was found to interfere with the red blood cell analysis method.

Thus, through empirical testing and analysis, it was found that the ionic surfactants (i.e., surfactants from all of the major classes having different electrostatic charges) tested in the rinse reagent formulation were not useful in the invention. In addition, nonionic surfactants, such as Brij® 35, and similar polyethoxylated alcohols and phenols, such as TritonX®-100, were not useful in the rinse reagent composition because they actively participate by attacking the white blood cells in the peroxidase method. It was eventually discovered that the nonionic Pluronic® surfactants, particularly Pluronic® P105, were not only compatible with the peroxidase method, but also were universally compatible with all of the hematological methods, and reaction mixtures used therein, performed on automated analyzers. Such Pluronic® surfactants provided clean sample runs and did not interfere with the sample contents, reaction mixtures, or final results.

In one aspect of the invention, the universal rinse reagent solution is used in the peroxidase method of white blood cell differential counting using automated hematology systems, as exemplified in Example 1. The same universal rinse reagent is also for use in automated methods to quantify and characterize red blood cells, platelets, and reticulocytes, and parameters related thereto, such as red cell volume, and hemoglobin analyses. The universal rinse reagent is further used in automated methods to quantify and characterize white blood cells, WBC, (also known as leukocytes), including lymphocytes, monocytes, neutrophils, eosinophils, and the like. In addition, the universal rinse reagent can be used in the basophil channel to facilitate the distinction between basophils and the nuclear lobularity of polymorphonuclear leukocytes.

The universal rinse may be used in methods for analyzing, quantifying, and determining the characteristics of both normal and abnormal blood cells, and for analyzing and determining all stages of cell development and differentiation in a particular cell lineage. Indeed, it will be appreciated by the skilled practitioner that the rinse reagent is applicable for all types of cellular analyses that are enumerated, identified, and/or determined by the various automated hematology analyzers, as well as improvements developed thereon.

It is envisioned that the universal rinse reagent as described herein is also compatible and useful with all types of wash reagent solutions that are routinely used by those in the art to remove or dissolve buildup of reagents, especially in certain channels and hardware components of automated hematology analyzers. By compatible is meant that no precipitation occurs in the rinse reagent solution or in the wash solution used. For example, alkaline hypochlorite ("bleach") and alkaline solutions containing 2-(2-ethoxyethoxy) ethanol are used as wash agents in the TECHNICON H●™ series of automated analyzers.

In another aspect, the universal rinse reagent will be able to replace one or more solutions that are presently used on automated hematology analyzers. Accordingly, the universal rinse reagent will advantageously streamline the automated process and alleviate the several changes of rinse containers that must be performed by the practitioner. A reduction in the number of reagents required on an automated system affords greater economy and efficiency to the analytical process, as well as improves and facilitates the upkeep and general maintenance of the system.

It will be appreciated by those skilled in the art that the invention may also be employed with stock calibrator, control and other solutions of blood cells which are specifically prepared to calibrate and maintain apparatus accuracy. The term "sample" without other modifiers as used herein is specifically intended to include either whole blood or other solutions which contain blood cells. Moreover, the subject matter of the invention may also apply to manual methods in combination with semi- or fully-automated methods as illustrated and described herein.

The following examples are illustrative of the invention. They are presented to further facilitate an understanding of the inventive concepts and in no way are to be interpreted as limiting the scope of the present invention.

EXAMPLES

EXAMPLE 1

This example demonstrates that the universal rinse reagent may be instrumental in improving the performance of the peroxidase method of white blood cell differential counting using an automated analyzer system as described hereinbelow.

Use of the disclosed universal rinse reagent in the peroxidase method of white blood cell differential counting is associated with the use of an aqueous reagent composition or diluent employed in the first reaction phase ("the R1 phase") of the peroxidase method (i.e., the red blood cell lysis and white blood cell fixing phase) that is formulated to contain two particular classes of surfactants: a nonionic surfactant and an anionic surfactant, described in co-pending patent application U.S. Ser. No. 08/442,491, filed concurrently herewith on May 16, 1995, and assigned to the assignee of the present invention, now U.S. Pat. No. 5,639, 630. Table 2 provides an example of the preferred components and their preferred respective concentrations and ranges in such a dual surfactant-containing R1 reagent composition (also called Px 1 herein) of the peroxidase ("Px") method of white blood cell differential counting. It will be appreciated by those in the art that the concentrations and ranges of each of the listed reagent components may deviate by about ±5% to 10% without adversely affecting the rinse composition. In addition, for each of the components of the rinse reagent composition as listed in Table 2, the preferred quantities per liter are provided in parenthesis, and are not intended to be limiting.

TABLE 2

| Component | Qty/L |
|---|---|
| Nonionic polyethoxylate surfactant<br>(e.g., Brij ® 35; Triton ® X-100) | 0.10 g–0.20 g<br>(0.12–0.14 g) |
| Ionic surfactant, either anionic (e.g., SDS)<br>or zwitterionic (e.g., TDAPS) | 0.085 g–0.115 g<br>(0.105 g) |
| Sugar or Sugar alcohol (e.g., sorbitol) | 110 g–120 g<br>(113.0 g) |
| NaPhosphate, monobasic | 1.98 g–2.18 g<br>(2.08 g) |
| NaPhosphate, dibasic | 11.30 g–12.5 g<br>(11.89 g) |
| Inorganic or alkali metal salt<br>(e.g., NaCl, KCl, or LiCl) | 0.4 g–0.6 g<br>(0.488 g) |
| Metal chelator (e.g., EDTA, EGTA,<br>di, tri, and tetrasodium EDTA or EGTA) | 0.675 g–0.825 g<br>(0.750 g) |
| Fixative (e.g., formaldehyde,<br>37 g/dL) | 50 g–60 g<br>(150 mL) |
| Deionized Water,<br>q.s. to | <br>1.00 L |
| pH | 6.9–7.6<br>(7.0–7.5) |

In practicing the peroxidase method in which use of the universal rinse reagent is particularly exemplified, the aqueous Px 1 reagent composition was rapidly mixed with the blood sample to be analyzed to form an R1 reaction mixture. Uniform mixture occurred within about S seconds of the time the Px 1 reagent solution and the blood sample come into contact with each other. If the Px 1 reaction composition and the sample are not uniformly and rapidly mixed, fixation (i.e., chemical crosslinking by formaldehyde) of the red blood cells will occur which prevents complete lysis of the red blood cells, thereby greatly impairing the accuracy of the differential WBC count obtained from the practice of the method. In other words, incomplete mixing will result in non-homogeneous fixation and lysis of red blood cells (i.e., these processes will not be uniformly carried out) and the method will yield inaccurate results. It is also noted that nonhomogeneous fixation of the white blood cells affords accurate results in the method.

When mixed, the Px 1 reagent solution and the blood sample were initially at room temperature (about 20° C. to about 28° C.) to ensure that the critical heating profile of the automated analyzer was maintained. The reaction mixture was then rapidly heated to a temperature of from about 62° C. to about 72° C., ideally from about 64° C. to about 68° C., by injection into the appropriate chamber(s) of an automated hematology analyzer maintained at a suitably elevated temperature. Kinetic measurements indicated that the reaction mixture temperature was brought to from about 35° C. to about 42° C. substantially immediately upon injection. The subsequent temperature rise began from that point. The heating of the reaction mixture occurred within about 15 seconds, preferably within about 20 seconds; if heating did not occur as rapidly, red blood cells will become chemically crosslinked, thereby preventing their lysis and interfering with the accuracy of the differential white blood cell count.

Immediately thereafter, a staining mixture comprising hydrogen peroxide and a suitable chromogen such as 4-chloro-1-naphthol was mixed with the reaction mixture. The initial temperature of the staining mixture was room temperature; the temperature after mixing the staining mixture with the reaction mixture was increased to from about 62° C. to about 72° C., preferably from about 63° C. to about 69° C., in a period of within about 30 seconds preferably from about 8 to 15 seconds, to stain the neutrophils, monocytes, and eosinophils which are peroxidase active.

With specific regard to an automated hematology analyzer of the TECHNICON H●™ series, the automated analyzer reaction chamber was maintained at a temperature of approximately 72° C. 12.0 μL of whole blood and 250 μL of the Px 1 reagent composition were simultaneously injected into the system at room temperature, thereby rapidly mixing the two to form the R1 reaction mixture, which was then incubated for up to about 30 seconds, during which time the temperature of the mixture was increased to from about 62° C. to about 72° C. By the end of the incubation period, the red blood cells were attacked by the surfactant and lysed resulting in the loss of substantially all of their hemoglobin content and their conversion to ghosts which were fixed. In addition, the white blood cells were fixed. Immediately thereafter, 125 μL of the chromogen reagent 8.0 g/L of 4-chloro-1-naphthol in oxydiethanol, was simultaneously injected with 250 μL of a hydrogen peroxide solution comprising 3.0 g/L hydrogen peroxide to form the R2 reaction mixture. Both reagents were initially at room temperature, but due to the temperature of the reaction chamber, the staining mixture temperature was increased to from about 63° C. to about 69° C. within about 30 seconds, at which time the peroxidase staining of neutrophils and eosinophils was completed. Approximately 0.5 to 1.0 mL of the universal rinse reagent was added to flush out all of the channels. About 0.6 seconds later, another 0.5 to 1.0 mL of the rinse solution was added for additional cleaning.

In particular, the rinse cycle of the peroxidase method performed on automated hematology analyzers of the TECHNICON H●™ series was formerly carried out using either a rinse reagent 1 solution and a rinse reagent 2 solution, which were found by the present inventors to cause several problems in the hematological methods used for analysis. The solution to these problems led to the discovery, development, and application of the universal rinse reagent as taught and described herein. Specifically, the ionic surfactant SDS in the previously used rinse reagent 1 solution was found to be incompatible with the cationic dye Oxazine 750, which is a component of the reagent used in the analysis of reticulocytes and red blood cells. This incompatibility was evidenced by the presence of a blue precipitate in selected loci of the reticulocyte channel.

Further and significantly, it was discovered by the present inventors that the nonionic surfactant Brij® 35, a component of the rinse reagent 2 solution, was a necessary and active component in the R1 phase of the peroxidase method. In this regard, it was discovered that Brij® 35 caused the lysis of red blood cells, but also was able to attack eosinophils in the sample if the rinse carryover volume exceeded about 10 μL (see U.S. Ser. No. 08/442,491, now U.S. Pat. No. 5,639,630 to M. Malin et al., filed concurrently herewith and assigned to the assignee of the present invention). Brij® 35 is a member of the class of nonionic surfactants that are straight chain aliphatic hydrophobes etherified to polyethylene glycol.

As it occurs, rinse carryover is variable from system to system; consequently, unwanted participation of surfactant such as Brij® 35 also varies from system to system. It should be appreciated that even when the volume of rinse carryover is constant, system-to-system variations in this volume constitute a cause of deviations in the performance of the method from system-to-system. To avoid the problem of variable rinse carryover in performing the peroxidase white blood cell differential method on automated analyzers, it was further discovered by the present inventors that surfactant used in the universal rinse reagent solution should be nonactive in the method and should not participate or function in the performance of the method, when present due to rinse carryover. In accordance with the invention and as described hereinbelow, the universal rinse reagent, which does not contain the same surfactants that are contained in the Px 1 reagent composition, was discovered and employed in the method.

An illustration of the problem of rinse carryover is as follows: about 7–10 μL (more specifically, 8.0+/−0.1 μL) of rinse solution is generally left over in the reaction chamber after completion of the intersample rinse cycle. If the rinse solution is formulated to contain the nonionic surfactant, Brij® 35, this small volume of rinse solution is responsible for adding an amount of Brij® 35 to the R1 phase of the peroxidase method which is required for acceptable red cell lysis and cell separation results on the cytogram. However, an excessive volume of rinse carryover, i.e., greater than or equal to about 10 μL, causes deterioration of the cytogram. Specifically, the eosinophil population migrates up into the neutrophil population of the cytogram, and both monocytes and lymphocytes move down in the cytogram (see FIG. 1D). When the volume of rinse carryover is about 13.3 μL, the peroxidase method is completely degraded by the presence of the nonionic surfactant Brij® 35. This particular problem is detailed in U.S. Ser. No. 08/442,491, now U.S. Pat. No. 5,639,630 to M. Malin et al., filed concurrently herewith.

Since the volume of the Px 1 reagent solution (containing nonionic surfactant such as Brij® 35) added during the R1 phase of the peroxidase method is 0.25 mL, the calculated Brij® 35 concentration during the first reaction phase of the peroxidase method is about 0.093 g/L to 0.120 g/L, which corresponds to a volume of rinse carryover of approximately 8.0 to 10.0 μL. When a Px 1 reagent composition containing both a nonionic surfactant and an ionic surfactant was used in conjunction with the universal rinse (in which Brij® 35 was eliminated), as disclosed herein, the variable amount of Brij® 35 delivered to the Px R1 phase was eliminated, and rinse carryover was insignificant (e.g., less than 1%); in addition, the accuracy and precision of the results were highly acceptable. Nonionic surfactant, i.e., Brij® 35, was determined by the present inventors to be the agent, which, if formulated into the universal rinse reagent solution and used in the peroxidase method, caused the degradation of the white cell cluster in the cytogram.

EXAMPLE 2

The efficacy and feasibility of the universal rinse for use in multiple, sequential sample analyses and for keeping an automated hematology system clean was determined in an experiment which incorporated a total of 1035 aspirations of whole blood over a period of two days. As shown in Table 3, the parameters of WBCP (i.e., white blood cell count), RBC, Hb, MCV, PLT, and WBCB were acceptable after 500, 700, and 1035 aspirations in the analyses of blood samples aged for about two days at room temperature. At least one parameter from each channel of the TECHNICON H●™ automated analyzer (i.e., H●™ in this particular example) was monitored: for the RBC/PLT channel: RBC, PLT, MCV; for the hemoglobin (Hb) channel: Hb; for the peroxidase channel: WBCP, the white blood cell count; and for the Basophil channel: WBCB, the basophil cell count.

After the last (i.e., the 1035th) aspiration, the system was inspected and it was found that the system was free of buildup. It is noted here that precautions should be taken to ensure that the entire hydraulic path for a given channel receives the universal rinse reagent solution during the performance of a method. However, if such channel buildup or debris accumulation does occur, it can be removed by utilizing a wash solution, for example, alkaline 2(2-ethoxyethoxy) ethanol containing a surfactant, in the system (about 10 cycles), followed by the use of the universal rinse reagent (about 10 cycles) to remove all traces of the wash solution components. This experiment showed that the universal rinse reagent kept the system clean enough up to about 1035 sample aspirations to allow acceptable performance of the methods.

A similar experiment performed on 2009 samples, involving an equal number of sample aspirations, was not successful because a significant amount of debris was deposited in the hydraulic path of the automated analyzer. Consequently, it was determined that the appropriate interval of using the universal rinse reagent before washing is needed is on the order of about 1000 to about 1050 aspirations.

In Table 3, the terms "LO", "MID", and "HI" refer to synthetic, commercially-available control materials used to calibrate automated systems; "sd" is the mean standard deviation from the analysis of ten replicate blood samples. In addition, "WBCP" refers to the parameter of the white blood cell count determined from the peroxidase method (peroxidase channel); "RBC" refers to the parameter of red blood cell count; "Hb" refers to the parameter of hemoglobin concentration; "MCV" refers to the parameter of mean cell volume; "PLT" refers to the parameter of platelet count; and "WBCB" refers to the parameter of the white blood cell count determined in the basophil channel. These abbreviations are standard and are known among those having skill in the art.

TABLE 3

| | | Universal Rinse | | | | | |
|---|---|---|---|---|---|---|---|
| | | CBC Parameter Recovery | | | | | |
| | Aspirations | WBCP | RBC | Hb | MCV | PLT | WBCB |
| Day 1 | | | | | | | |
| Whole Blood Sample | | 5.09 | 4.35 | 12.8 | 91 | 291 | 4.72 |

TABLE 3-continued

| | Universal Rinse | | | | | | |
|---|---|---|---|---|---|---|---|
| | | CBC Parameter Recovery | | | | | |
| | Aspirations | WBCP | RBC | Hb | MCV | PLT | WBCB |
| (sd) | | 0.11 | 0.03 | 0.05 | 0.6 | 6 | 0.08 |
| LO | 0 | 3.41 | 2.39 | 5.7 | 72.6 | 75 | 3.36 |
| (sd) | | 0.09 | 0.012 | 0 | 0.2 | 2 | 0.07 |
| MID | 0 | 7.53 | 4.5 | 13 | 85.7 | 223 | 7.51 |
| (sd) | | 0.11 | 0.12 | 0 | 0.4 | 1 | 0.15 |
| HI | 0 | 19.3 | 5.45 | 16.9 | 89.1 | 471 | 18.9 |
| (sd) | | 0.92 | 0.06 | 0.3 | 0.2 | 12 | 0.7 |
| Day 1 | | | | | | | |
| Whole Blood Sample | | 5.01 | 4.21 | 12.9 | 90.6 | 300 | 4.69 |
| (sd) | | 0.12 | 0.04 | 0.08 | 0.6 | 7 | 0.13 |
| LO | 500 | 3.38 | 2.33 | 5.7 | 72.4 | 75 | 3.35 |
| (sd) | | 0.06 | 0.02 | 0.06 | 0.06 | 3 | 0.02 |
| MID | 500 | 7.63 | 4.43 | 13 | 84.3 | 221 | 7.51 |
| (sd) | | 0.07 | 0.03 | 0.05 | 0.19 | 5 | 0.12 |
| HI | 500 | 19.23 | 5.35 | 17 | 88.4 | 462 | 18.65 |
| (sd) | | 0.16 | 0.03 | 0.1 | 0.3 | 11 | 0.15 |
| Day 2 | | | | | | | |
| Whole Blood Sample | | 5.92 | 4.22 | 13 | 89.1 | 188 | 5.62 |
| (sd) | | 0.11 | 0.03 | 0.05 | 0.3 | 5 | 0.1 |
| LO | 700 | 3.43 | 2.33 | 5.6 | 71.7 | 75 | 3.34 |
| (sd) | | 0.02 | 0.02 | 0.06 | 0.2 | 3 | 0.12 |
| MID | 700 | 7.5 | 4.43 | 13 | 83.9 | 224 | 7.86 |
| (sd) | | 0.08 | 0.02 | 0 | 0.1 | 3 | 0.26 |
| HI | 700 | 19.07 | 5.35 | 17 | 87.9 | 458 | 18.68 |
| (sd) | | 0.59 | 0.04 | 0.05 | 0.1 | 12 | 0.84 |
| Day 2 | | | | | | | |
| Whole Blood Sample | | 6.06 | 4.2 | 13.1 | 88.8 | 185 | 5.78 |
| (sd) | | 0.13 | 0.02 | 0 | 0.4 | 4 | 0.08 |
| LO | 1035 | 3.29 | 2.31 | 5.6 | 72 | 72 | 3.28 |
| (sd) | | 0.02 | 0.01 | 0 | 0.4 | 5 | 0.02 |
| MID | 1035 | 7.43 | 4.36 | 12.9 | 84.2 | 214 | 7.44 |
| (sd) | | 0.14 | 0.02 | 0.1 | 0.4 | 4 | 0.16 |
| HI | 1035 | 18.57 | 5.23 | 16.8 | 88.4 | 467 | 18.61 |
| (sd) | | 0.3 | 0.03 | 0.1 | 0.3 | 10 | 0.8 |

EXAMPLE 3

The universal rinse was prepared and used in accordance with the invention in the analysis of reticulocytes performed on an automated hematology analyzer (i.e., the TECHNICON H●3™ analyzer, also referred to as the Miles H*3™ blood analyzer) in a method for analyzing reticulocytes in a whole blood sample. The "H*3™ reticulocyte method" (C. Brugnara et al, 1994, Am. J. Clin. Path., 102:623–632) detects the presence of reticulocytes (immature erythrocytes) in whole blood samples. The H*3™ method conventionally is carried out using an intersample rinse (Rinse 1) comprising: SDS at a concentration of 0.0318 g/L; TRIS base at a concentration of 6.60 g/L; $Na_2$EDTA dihydrate at a concentration of 1.00 g/L; 3.50 mL of concentrated HCl; NaCl at a concentration of 6.20 g/L, and a pH of 7.2±0.2. The H*3™ reticulocyte reagent contains the dye Oxazine 750 (5 mg/L) which stains RNA in reticulocytes. Since mature erythrocytes do not contain RNA, this difference provides a specific molecular target for the method and allows the determination of only reticulocytes in the method.

The performance of the standard H*3™ reticulocyte method performance was compared with that of a H*3™ reticulocyte method modified by substituting the universal rinse composition of the invention for the standard method rinse described above. The sample set included 30 normal, non-hospital samples and 29 hospital samples. The standard H*3™ method was performed on an H*3™ system as described in Brugnara et al., 1994. The modified method was performed on an H*3™ system in which Rinse 1 was replaced by the universal rinse in described by the invention. The results are presented in Table 4 below in which "R" is the correlation coefficient; "$S_{y.x}$" is the standard error of estimate; and "$x_{bar}-y_{bar}$" at is the difference between the sample set means for the reference method minus the test method.

The results of the reticulocyte analyses as shown in Table 4 demonstrate that all three parameters were within the specifications of the standard method. Therefore, the H*3™ reticulocyte method performed in an acceptable manner with the inclusion of the universal rinse in the method.

TABLE 4

| Automated Reticulocyte Method | R | $S_{y,x}$ | $x_{bar}-y_{bar}$ |
|---|---|---|---|
| Standard H*3 ™ Values Versus H*3 ™ Values Obtained Using Universal Rinse Reagent Composition of the Invention | 0.982 | 0.08 | −0.17 |
| H*3 ™ Specifications | >0.95 | <1.5 | <0.5 |

The contents of all patent applications, issued patents, published articles and references, and textbooks as cited herein are hereby incorporated by reference in their entirety.

As various changes can be made in the above compositions and methods without departing from the scope and spirit of the invention, it is intended that all subject matter contained in the above description, shown in the accompanying drawings, or defined in the appended claims will be interpreted as illustrative, and not in a limiting sense.

What is claimed is:

1. A method for preventing blood sample and reagent mixture accumulation inside system hardware and in all cell flow channels and system components of a semi- or fully-automated hematology analyzer used in blood sample analysis, after a blood sample has been analyzed in the hematology analyzer and before analysis of another blood sample therein, comprising:

a) mixing an aqueous reagent composition comprising the following components to form a rinsing and cleansing reagent solution: I) a nonionic nonhemolytic surfactant which is a block copolymer of polyoxyethylene and polyoxypropylene terminating in primary hydroxyl groups, wherein the weight percentage of polyoxyethylene is from about 20 to about 80 percent in a molecule of said surfactant, and the polyoxypropylene in said surfactant has a weight range of about 2000 to about 4000 g/mol; and ii) a buffer or buffer mixture at a concentration effective for maintaining an approximately neutral pH of said reagent solution; wherein said reagent solution rinses and removes unlysed cells, lysed cells and released intracellular contents thereof, and residual reagent components from all blood cell channels and system hardware of said hematology analyzer between blood sample analysis, thereby preventing sample carryover; and b) rinsing and removing lysed blood cells, released contents thereof, unlysed blood cells and reagent mixture accumulation from all blood cell channels of said analyzer and inside all system hardware and components thereof by contacting all said blood cell channels, system hardware and components thereof with the rinsing and cleansing reagent solution of step a) after the analysis of blood sample in said analyzer, before the analysis of another blood sample.

2. The method according to claim 1, wherein, in said reagent composition of step (a), the nonionic nonhemolytic surfactant has a weight percentage of polyoxyethylene of from about 30 to about 70 percent in said surfactant molecule.

3. The method according to claim 1, wherein, in said reagent composition of step (a), the nonionic nonhemolytic surfactant has a weight percentage of polyoxyethylene of about 50 percent in said surfactant molecule.

4. The method according to claim 1, wherein, in said reagent composition of step (a), the nonionic nonhemolytic surfactant has an average molecular weight selected from the group consisting of about 4200, 4600, 4950, 5900, 5750 and 6500 g/mol.

5. The method according to claim 1, wherein said nonionic nonhomolytic surfactant has an average molecular weight of about 6500 and has a weight percentage of polyoxyethylene of about 50 percent.

6. The method according to claim 1, wherein said buffer or buffer mixture maintains a pH of said risen reagent solution at from about 7.0 to about 7.3.

7. The method according to claim 1, wherein said buffer or buffer mixture comprises $Na_2HPO_4$, or a mixture thereof.

8. The method according to claim 1, wherein, in step (a), the buffer or buffer mixture maintains the pH of the rinse reagent solution at from about 6.8 to about 7.8.

9. The method according to claim 1, wherein said aqueous reagent composition of step a) further comprises an alkali metal chloride salt.

10. The method according to claim 9, where said alkali metal chloride salt is NaCl, KCl, or LiCl.

11. The method according to claim 10, wherein said alkali metal chloride salt is NaCl.

12. The method according to claim 1, wherein said aqueous reagent composition of said step a) further comprises an anti-microbial compound.

13. The method according to claim 12, wherein said anti-microbial compound is selected from the group consisting of 2-methyl-4-isothiazolin-3-one, 5-chloro-2-methyl-4-isothiazolin-3-one, N,N'-methylenebis (N'-(1-(hydroxymethyl)-2,5-dioxo-4-imidazolidinyl) urea, 1-(3-chloroallyl)-3,5,7-triaza-1-azoniaadamantane chloride, and 2-bromo-2-nitropropane-1,3-diol ($C_3H_6BrNO_4$).

14. The method according to claim 1, wherein said aqueous reagent composition of said step a) further comprises an anti-oxidant compound.

15. The method according to claim 14, wherein said anti-oxidant is selected from the group consisting of 3,3'-thiodiproprionic acid, 3,3'-dithioacetic acid, water-soluble vitamin E, butylated hydroxytoluene (BHT), 2, 6-di-tert-butyl-4-methylphenol, butylated hydroxyanisole (BHA), 2-tert-butyl-4-methoxyphenol, and ρ-methoxyphenol.

16. The method according to claim 1, wherein said aqueous reagent composition of said step a) has an osmolality from about 285 m Osmol/kg to about 305 mOsmol/kg.

17. The method according to claim 1, wherein, in step (b), the blood cell channels rinsed by said reagent include red blood cell/platelet channel, reticulocyte channel, basophil channel, peroxidase channel and hemoglobin channel.

18. A method for removing blood sample and reagent mixtures from inside of system components of semi- and fully-automated hematology analyzers used in the analysis of blood samples, comprising rinsing the insides of said hematology analyzer components including all blood cell analysis channels within said analyzer with an aqueous rinse reagent composition at least once after performing said hematology analysis, said rinse composition comprising: a nonionic nonhemolytic surfactant which is a block copolymer of polyoxyethylene and polyoxypropylene termination in primary hydroxyl groups, the weight percentage of said polyoxyethylene being from about 20 to about 80 percent in a molecule of said surfactant and a buffer or buffer mixture present at a concentration effective for maintaining an approximately neutral pH of the rinse composition.

19. The method according to claim 18, wherein, in said reagent composition of step (a), the nonionic nonhemolytic surfactant has a weight percentage of polyoxyethylene of from about 30 to about 70 percent in said surfactant molecule.

20. The method according to claim 18, wherein, in said reagent composition of step (a), the nonionic nonhemolytic surfactant has a weight percentage of polyoxyethylene of about 50 percent in said surfactant molecule.

21. The method according to claim 18, wherein, in said reagent composition of step (a), the nonionic nonhemolytic surfactant has an average molecular weight selected from the group consisting of about 4200, 4600, 4950, 5900, 5750 and 6500 g/mol.

22. The method according to claim 18, wherein said nonionic nonhemolytic surfactant has an average molecular weight of about 6500 and has a weight percentage of polyoxyethylene of about 50 percent.

23. The method according to claim 18, wherein the polyoxypropylene in the nonionic nonhemolytic surfactant has a weight range of about 2000 to about 4000 g/mol.

24. The method according to claim 18, wherein said rinse reagent composition further comprises a buffer or buffer mixture which maintains a pH of from about 6.8 to about 7.8.

25. The method according to claim 18, wherein said rinse reagent composition further comprises a buffer or buffer mixture which maintains a pH of from about 7.0 to about 7.3.

26. The method according to claim 20 or claim 25, wherein said buffer comprises $Na_2HPO_4$, $NaH_2PO_4$, or a mixture thereof.

27. The method according to claim 18, wherein said aqueous rinse reagent composition further comprises an alkali metal chloride salt.

28. The method according to claim 27, wherein said alkali metal chloride salt is NaCl, KCl, or LiCl.

29. The method according to claim 27, wherein said alkali metal chloride salt is NaCl.

30. The method according to claim 18, wherein said aqueous rinse reagent composition further comprises an anti-microbial compound.

31. The method according to claim 30, wherein said anti-microbial compound is selected from the group consisting of 2-methyl-4-isothiazolin-3-one, 5-chloro-2-methyl-4-isothiazolin-3-one, N,N'-methylenebis (N'-(1-(hydroxymethyl)-2,5-dioxo-4-imidazolidinyl) urea, 1-(3-chloroallyl)-3,5,7-triaza-1-azoniaadamantane chloride, and 2-bromo-2-nitropropane-1,3-diol ($C_3H_6BrNO_4$).

32. The method according to claim 18, wherein said aqueous rinse reagent composition further comprises an anti-oxidant compound.

33. The method according to claim 32, wherein said anti-oxidant is selected from the group consisting of 3,3'-thiodiproprionic acid, 3,3'-dithioacetic acid, water-soluble vitamin E, butylated hydroxytoluene (BHT), 2, 6-di-tert-butyl-4-methylphenol, butylated hydroxyanisole (BHA), 2-tert-butyl-4-methoxyphenol, and ρ-methoxyphenol.

34. The method according to claim 18, wherein said aqueous rinse reagent composition has an osmolality from about 285 m Osmol/kg to about 305 mOsmol/kg.

35. The method according to claim 18, wherein the blood cell channels rinsed by said reagent include red blood cell/platelet channel, reticulocyte channel, basophil channel, peroxidase channel and hemoglobin channel.

* * * * *